United States Patent [19]

Kawano et al.

[11] 4,305,931

[45] Dec. 15, 1981

[54] POWDERED COMPRESSED COSMETIC MATERIAL

[75] Inventors: Junichi Kawano, Sakura; Toshiaki Utsugi, Tokyo; Shigeo Inoue, Ichikai, all of Japan; Shizuo Hayashi, deceased, late of Sugito, Japan, by Horuko Hayashi

[73] Assignee: Kao Soap Co., Ltd., Tokyo, Japan

[21] Appl. No.: 78,156

[22] Filed: Sep. 24, 1979

[30] Foreign Application Priority Data

Sep. 29, 1978 [JP] Japan ................ 53-120273

[51] Int. Cl.$^3$ .............. A61K 7/031; A61K 7/032; A61K 7/035
[52] U.S. Cl. ........................... 424/69; 424/63
[58] Field of Search ................ 424/69, 63; 536/116, 536/115, 119

[56] References Cited

U.S. PATENT DOCUMENTS

| | | | |
|---|---|---|---|
| 1,320,855 | 11/1919 | Henderson | 424/DIG. 5 |
| 2,422,633 | 6/1947 | Petersen | 536/119 |
| 2,450,079 | 9/1948 | Brown | 536/116 |
| 2,626,257 | 1/1953 | Caldwell et al. | 424/69 X |
| 2,626,935 | 1/1953 | DeGroate | 536/116 |
| 2,908,681 | 10/1959 | Anderson et al. | 536/116 |
| 3,102,114 | 8/1963 | Komori et al. | 536/116 |
| 3,972,997 | 8/1976 | Nakashio et al. | 424/69 |
| 4,032,702 | 6/1977 | James | 536/115 |
| 4,159,318 | 6/1979 | Mausner et al. | 424/69 |

FOREIGN PATENT DOCUMENTS 575857  5/1924  France ................ 424/69

*Primary Examiner*—Dale R. Ore

*Attorney, Agent, or Firm*—Oblon, Fisher, Spivak, McClelland & Maier

[57] ABSTRACT

A powdered compressed cosmetic material comprising a hydroxypropyl-etherified glycolipid ester represented by the general formula;

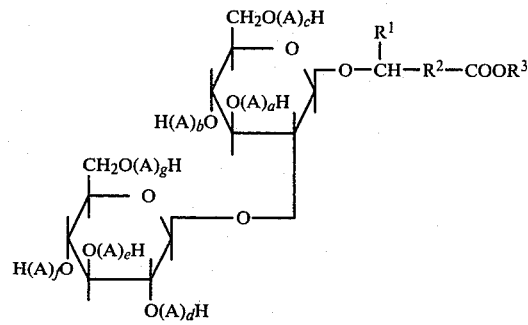

wherein $R^1$ represents a methyl group or a hydrogen atom, $R^2$ represents a saturated or unsaturated hydrocarbon group having carbon atoms of 11 to 15 when $R^1$ is a methyl group, or $R^2$ represents a saturated or unsaturated hydrocarbon group having carbon atoms of 12 to 16 when $R^1$ is a hydrogen atom, A represents the group

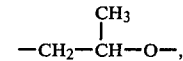

$R^3$ represents a saturated or unsaturated hydrocarbon group having carbon atoms of 1 to 20 or $-(A)_hH$, and a, b, c, d, e, f, g and h are integers, whose sum ranges from 1 to 6.

2 Claims, No Drawings

POWDERED COMPRESSED COSMETIC MATERIAL

BACKGROUND OF THE INVENTION

1. Field of the Invention

This invention relates to powdered compressed cosmetics, more particularly to a novel powdered compressed cosmetic material comprising a hydroxypropyl-etherified glycolipid ester (hereinafter abbreviated as "POSL") represented by the general formula (I);

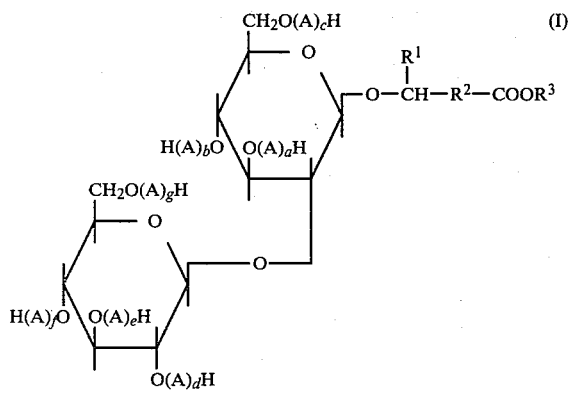

wherein $R^1$ represents a methyl group or a hydrogen atom, $R^2$ represents a saturated or unsaturated hydrocarbon group having carbon atoms of 11 to 15 when $R^1$ is a methyl group, or $R^2$ represents a saturated or unsaturated hydrocarbon group having carbon atoms of 12 to 16 when $R^1$ is a hydrogen atom, A represents the group

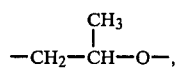

$R^3$ represents a saturated or unsaturated hydrocarbon group having carbon atoms of 1 to 20 or $-(A)_hH$, and a, b, c, d, e, f, g and h are integers, whose sum ranges from 1 to 60.

2. Description of the Prior Art

Powdered compressed cosmetic materials have hithertofore been produced by compressing and molding under elevated pressure a mixture of a major component such as talc or sericite, and a combining agent such as a paste, for instance, carboxymethyl cellulose, or an emulsifying agent, for instance, squalane or lanolin. However, these known cosmetic materials, which are usually produced by compression to such extent that applicable hardness can be obtained, are liable to be easily cracked when dried or fallen by mistake while being carried with the consumer, with eventual unfitness for use.

In order to eliminate the above noted defects, the present inventors have made a wide variety of studies, and as a result, have found that a powdered compressed cosmetic material of good and stable quality and performance can be produced by incorporating POSL of the formula (I) in the cosmetic composition.

Based on this finding, the present invention has been accomplished.

SUMMARY OF THE INVENTION

Briefly stated, this invention provides an excellent powdered compressed cosmetic material which comprises POSL represented by the formula (I) and which is prevented against cracking even when dried or given a shock.

DETAILED DESCRIPTION OF THE PREFERRED EMBODIMENTS

POSL to be used in the present invention is a novel compund which can be produced, for instance, by reacting glycolipid or a glycolipid ester represented by the general formula (II);

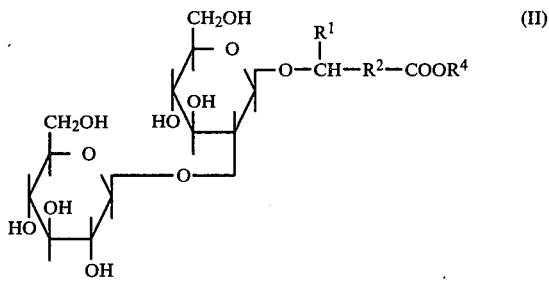

wherein $R^4$ represents a saturated or unsaturated hydrocarbon group having carbon atoms of 1 to 20 or a hydrogen atom, $R^1$ and $R^2$ are the same as defined above, with propylene oxide in the presence of an alkali catalyst (Japanese Patent Application No. 24306/1978 now U.S. Pat. No. 4,195,177, issued Mar. 25, 1980).

The properties of POSL which is useful in and typical of the invention are shown below.

| $R^1$ | $R^2$ | $R^3$ | Addition mole number | Hydroxyl value | Acid value | Saponification value | Appearance |
|---|---|---|---|---|---|---|---|
| CH3 | C15H28 | CH3 | 5 | 420.3 | 0.2 | 61.3 | |
| | | | 7 | 376.5 | 0.7 | 53.5 | Viscous paste substance |
| | | | 15 | 261.5 | 0.3 | 37.0 | |
| | | | 30 | 167.2 | 1.2 | 21.5 | |
| CH3 | C15H28 | C12H25 | 7 | 325.3 | 0.2 | 47.0 | Paste-like wax substance |
| | | | 15 | 236.2 | 0.8 | 31.5 | |
| | | | 30 | 159.3 | 0.5 | 20.7 | |
| CH3 | C15H28 | $-(A)_hH$ | 5 | 492.0 | 0.7 | 60.5 | |
| | | | 8 | 413.5 | 0.0 | 51.5 | Viscous paste substance |
| | | | 15 | 299.0 | 0.1 | 37.5 | |
| | | | 30 | 185.3 | 0.0 | 23.8 | |

By the term powdered compressed cosmetic material is meant the so-called pressed face powder, cheek rouge, highlight, eye-shadow or the like for use with a compact which is produced by mixing a major component such as talc, kaolin, sericite, silk powder, nylon powder, metal soap, starch or the like, with a combining agent such as a paste, oil or emulsion, for instance, squalane, liquid paraffin, isopropyl myristate, oleyl alcohol, lanolin or the like, and further incorporating an inorganic or organic pigment in the above mixture, and finally subjecting the resulting mixture to compression molding.

The powdered compressed cosmetic material according to the present invention can be produced by any conventional dry or wet method, with the exception that POSL is mixed with the above composition in an amount of 0.1 to 10 percent, preferably 3 to 7 percent, based upon the total weight of the powdered compressed cosmetic material.

This invention will now described with reference to certain specific Examples, but the invention is not limited to the Examples. The following Reference Example is illustrative of the preparation of POSL which is useful in the invention.

REFERENCE EXAMPLE (i) To a mixture of 1500 g of glucose, 75 g of a yeast extract and 15 g of urea was added water to adjust the whole volume to 15 l, and the resulting mixture was sterilized and utilized as a fermentation liquid. To this fermentation liquid was inoculated *Torulopsis bombicola* which had been cultured in the same culture medium as above at 30° C. for 48 hours. The fermentation was started under the following conditions: temperature, 20° C.; stirring, 300 rpm; and aeration, 0.33 VVM. The culturation was conducted for 24 hours after inoculation of the microorganisms, and 150 g of beef tallow was added, followed by adding the same amount of beef tallow at intervals of 24 hours. The added beef tallow amounted to 900 g. After the final addition, the fermentation was continued for additional 24 hours. The fermentation time amounted to 168 hours. After the completion of the fermentation, the sophorolipid layer precipitating at the bottom of a fermentor was collected by decantation to give 1300 g of sophorolipid, which was in the form of a paste having a water content of about 50%.

(II) 100 g of the thus obtained sophorolipid together with 2.5 g of polypropylene glycol having an average molecular weight of 200 was placed in a 200 ml round bottom flask equipped with a stirrer and a Liebig condenser. The mixture was evaporated with stirring an an oil bath (80° C.) under a reduced pressure of 250 mmHg to eliminate water. 2 hours later, the distillation of water was completed, and the water content at that time was found to be less 1%.

(iii) 150 g of methanol was added to the thus prepared polypropylene solution of sophorolipid, and to the resulting mixture was added 2.5 g of sulfuric acid. The mixture was reacted at 40° C.±2° C. for 90 minutes. The reaction was regarded as having been completed at the time when many spots of the raw material or sophorolipid converged on one spot corresponding to a glycolipid methyl ester by thin-layer chromatography on silica gel [developing solvent: chloroform-methanol-acetic acid (75:20:5)].

After the completion of the reaction, the mixture was made neutral with a given amount of potassium hydroxide and then filtered. The filtrate was placed again in a round bottom flask equipped with a Liebig condenser, and methanol and methyl acetate were removed by distillation to obtain 48 g of a mixture containing 94% of a crude [2'-O-β-D-glucopyranosyl-β-D-glucopyranosyl)oxy]alkanic acid and alkenic acid methyl ester in the form of a brown paste and coexisting polypropylene glucose. This mixture was purified by column chromatography on silica gel to obtain a pure [(2'-O-β-D-glucopyranosyl-β-D-glucopyranosyl)oxy]alkanic acid and alkenic acid methyl ester.

| IR (cm$^{-1}$): | 1740 ($>$C=O ester) |  |
|---|---|---|
|  | 1380–3200 (—OH sugar) |  |
|  | 900–750 (glucopyranose ring) |  |
| NMR [δ(pyridine)]: | 1.1–1.6 (—CH$_2$—CH$_2$—) |  |
|  | 3.6 (—O—CH$_3$) |  |
|  | 3.5–5.0 (sugar) |  |
|  | 5.5 (—CH=CH— unsaturated fatty acid) |  |
| Oil-characteristics analysis: | Acid value: | 0 |
|  | Hydroxy value: | 615 |
|  | Saponification value: | 88 |
|  | Ester value: | 87 |

(iv) Into an autoclave were placed 100 g of the thus obtained mixture of the [(2'-O-β-D-glucopyranosyl-β-D-glucopyranosyl)oxy]alkanic acid and alkenic acid methyl ester and coexisting polypropylene glycol and 0.25 g of potassium hydroxide. Subsequently, propylene oxide gas was bubbled into the mixture in an amount corresponding to a predetermined addition mole number, and the mixture was reacted at 100°–120° C. for 6 hours. After the completion of the reaction, the mixture was neutralized with phosphoric acid and filtered under high pressure to obtain a crude product in the form of a brown paste. This product was purified by chromatography on silica gel to obtain a pure polyoxypropylene[(2'-O-β-D-glucopyranosyl-β-D-glucopyranosyl)oxy]alkalic acid and alkenic acid methyl ester as a pale yellow paste.

EXAMPLE 1

Test samples A to D were prepared according to the compositions and preparation methods indicated below. After these test samples and commercial goods E and F were preserved at 50° C. for 12 hours, any cracks arising from drying were observed with the naked eye.

The results obtained are shown in Table 1. From these results, it can be seen that the samples C and D produced by the present method have nothing defective and are stable.

| Samples | Kinds | Compositions (%) | | Preparation methods |
|---|---|---|---|---|
| A | Conventional formulation | Talc | 60 | Dry method Compressive pressure: 50 kg/cm$^2$ |
|  |  | Sericite | 20 |  |
|  |  | Koalin | 10 |  |
|  |  | Aluminum stearate | 2 |  |
|  |  | Lanolin | 2 |  |
|  |  | Squalane | 3 |  |
|  |  | Titanium oxide | 2 |  |
|  |  | Iron oxide | 1 |  |
| B | Conventional formulation | Talc | 70 | Wet method Compressive pressure: 40 kg/cm$^2$ |
|  |  | Tericite | 25 |  |
|  |  | Aluminum stearate | 2 |  |
|  |  | Titanium oxide | 2 |  |
|  |  | Iron oxide | 1 |  |
|  |  | 0.1% Carboxymethyl cellulose | 20 |  |
| C | Applicants' formulation | Talc | 75 | Dry method Compressive pressure: 40 kg/cm$^2$ |
|  |  | Sericite | 16 |  |
|  |  | Aluminium stearate | 2 |  |
|  |  | POSL-1 | 4 |  |

-continued

| Samples | Kinds | Compositions (%) | | Preparation methods |
|---|---|---|---|---|
| D | Applicants' formulation | Titanium oxide | 2 | Wet method Compressive pressure: 40 kg/cm$^2$ |
| | | Iron oxide | 1 | |
| | | Talc | 80 | |
| | | Kaolin | 8 | |
| | | Aluminium stearate | 3 | |
| | | POSL-2 | 6 | |
| E | | Titanium oxide | 2 | |
| | | Iron oxide | 1 | |
| | | Commercial solid face powder | | |
| F | | Commercial cheek rouge | | |

POSL-1: $R^1 = CH_3$, $R^2 = C_{15}H_{28}$, $R^3 = C_{12}H_{25}$ the sum of a to h = 7 in the formula (I)
POSL-2: $R^1 = CH_3$, $R^2 = C_{15}H_{28}$, $R^3 = -(A)_hH$ the sum of a to h = 15 in the formula (I)

TABLE 1

| Sample marks | Cracked conditions |
|---|---|
| A | Cracked and exfoliated partly |
| B | Cracked |
| C | Not cracked nor exfoliated |
| D | Not cracked nor exfoliated |
| E | Cracked |
| F | Cracked and exfoliated partly |

EXAMPLE 2

The same samples A to F as used in Example 1 were placed in compacts, and the compacts were each dropped ten times naturally from a distance or height of 1.5 m. Any cracks caused by such falling test were observed with the naked eye.

The results obtained are shown in Table 2. From these results, it can be seen that the samples C and D produced by the present method were unaffected by the test and were found to retain their stability.

TABLE 2

| Samples | Cracked conditions |
|---|---|
| A | Cracked and exfoliated almost wholly from the compact |
| B | Cracked and exfoliated partly from the compact |
| C | Not cracked nor exfoliated |
| D | Not cracked nor exfoliated |
| E | Cracked and exfoliated partly from the compact |
| F | Cracked and exfoliated almost wholly from the compact |

EXAMPLE 3

Four species A to D extracted from the same samples as used in Example 1 and two species G and H freshly prepared by the present method were cut off in a region of 3 cm×3 cm, respectively. These samples were each placed horizontally and given a stress of 5 kg/cm$^2$ from a horizontal direction at a rate of 5 mm/minute until any cracks were caused. The distance (mm×10) by which the dynamic point migrated was measured.

The results obtained are shown in Table 3. From these results, it can be seen that the migration distance of the present samples is large, which indicates these samples are resistant to deformation and stable.

TABLE 3

| Samples | Test runs | | | | | Average values |
|---|---|---|---|---|---|---|
| | 1st | 2nd | 3rd | 4th | 5th | |
| A | 30 | 33 | 28 | 29 | 32 | 30.4 |
| B | 28 | 27 | 29 | 32 | 31 | 29.4 |
| C | 45 | 42 | 44 | 43 | 42 | 43.2 |
| D | 41 | 42 | 41 | 41 | 43 | 41.6 |
| G | 39 | 41 | 42 | 39 | 40 | 40.2 |
| H | 40 | 41 | 39 | 42 | 42 | 40.8 |

Compositions of Samples G and H

| Compositions | Samples | |
|---|---|---|
| | G | H |
| Talc | 56 parts | 65 parts |
| Sericite | 20 | 16 |
| Aluminium stearate | 2 | 2 |
| Titanium oxide | 2 | 2 |
| Iron oxide | 1 | 1 |
| Kaolin | 10 | 8 |
| Lanolin | 2 | 1 |
| Squalane | 3 | 2 |
| POSL-3 | 4 | — |
| POSL-4 | — | 3 |
| Preparation method | Dry method | Dry method |
| Compressive pressure | 40 kg/cm$^2$ | 40 kg/cm$^2$ |

POSL-3: $R^1 = CH_3$, $R^2 = C_{15}H_{28}$, $R^3 = CH_3$ the sum of a to h = 30 in the formula (I)
POSL-4: $R^1 = CH_3$, $R^2 = C_{15}H_{28}$, $R^3 = -(A)_hH$ the sum of a to h = 5 in the formula (I)

What we claim is:

1. A compressed powdered cosmetic for use with a compact selected from the group consisting of face powder, cheek rouge, highlight and eye shadow, containing from 0.1 to 10% by weight of a hydroxypropyl-etherified glycolipid ester represented by the general formula:

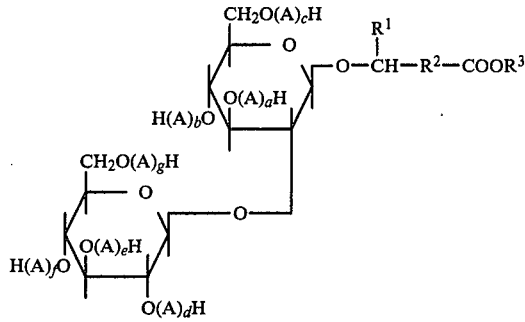

wherein $R^1$ represents a methyl group or a hydrogen atom, $R^2$ represents a saturated or unsaturated hydrocarbon group having carbon atoms of 11 to 15 when $R^1$ is a methyl group, or $R^2$ represents a saturated or unsaturated hydrocarbon group having carbon atoms of 12 to 16 when $R^1$ is a hydrogen atom, A represents the group

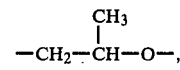

$R^3$ represents a saturated or unsaturated hydrocarbon group having carbon atoms of 1 to 20 or $-(A)_hH$, and a, b, c, d, e, f, g and h are integers, whose sum ranges from 1 to 60.

2. The compressed powdered cosmetic composition of claim 1, containing from 3 to 7% by weight of the hydroxypropyl-etherified glycolipid ester.

* * * * *